(12) United States Patent
Frake

(10) Patent No.: US 8,357,162 B2
(45) Date of Patent: Jan. 22, 2013

(54) INTRAMEDULLARY MANDIBULAR CONDYLE IMPLANTS AND METHOD FOR APPLICATION OF THE SAME

(76) Inventor: Paul Christopher Frake, Arlington, VA (US)

( * ) Notice: Subject to any disclaimer, the term of this patent is extended or adjusted under 35 U.S.C. 154(b) by 144 days.

(21) Appl. No.: 13/004,015

(22) Filed: Jan. 10, 2011

(65) Prior Publication Data

US 2011/0172668 A1 Jul. 14, 2011

Related U.S. Application Data

(60) Provisional application No. 61/335,820, filed on Jan. 13, 2010.

(51) Int. Cl.
*A61B 17/56* (2006.01)
(52) U.S. Cl. ........................................ 606/62
(58) Field of Classification Search ............. 606/60–68, 606/54, 57, 105
See application file for complete search history.

(56) References Cited

U.S. PATENT DOCUMENTS

| | | | | |
|---|---|---|---|---|
| 2,588,006 A | * | 3/1952 | Hufnagel | 433/123 |
| 2,614,559 A | * | 10/1952 | Livingston | 606/64 |
| 2,672,861 A | * | 3/1954 | Jonas et al. | 606/63 |
| 2,985,168 A | * | 5/1961 | Jonas et al. | 606/96 |
| 3,118,444 A | * | 1/1964 | Serrato, Jr. | 606/62 |
| 3,623,164 A | * | 11/1971 | Bokros | 606/60 |
| 3,744,488 A | * | 7/1973 | Cox | 606/64 |
| 4,016,874 A | * | 4/1977 | Maffei et al. | 606/62 |
| 4,232,660 A | * | 11/1980 | Coles | 600/210 |
| 4,433,677 A | * | 2/1984 | Ulrich et al. | 606/250 |
| 4,554,914 A | * | 11/1985 | Kapp et al. | 606/86 A |
| 4,636,215 A | * | 1/1987 | Schwartz | 623/17.17 |
| 4,858,601 A | * | 8/1989 | Glisson | 606/916 |
| 4,898,186 A | * | 2/1990 | Ikada et al. | 606/62 |
| RE33,348 E | * | 9/1990 | Lower | 606/65 |
| 5,217,462 A | * | 6/1993 | Asnis et al. | 606/916 |
| 5,626,583 A | | 5/1997 | Davis, Jr. | |
| 5,810,812 A | * | 9/1998 | Chin | 606/53 |
| 5,827,285 A | * | 10/1998 | Bramlet | 606/60 |
| 5,964,768 A | * | 10/1999 | Huebner | 606/317 |
| 6,197,029 B1 | | 3/2001 | Fujimori et al. | |
| 6,547,791 B1 | | 4/2003 | Buhren et al. | |
| 6,607,531 B2 | | 8/2003 | Frigg | |
| 6,730,090 B2 | | 5/2004 | Orbay et al. | |
| 7,625,395 B2 | * | 12/2009 | Muckter | 606/300 |
| 7,722,611 B2 | | 5/2010 | Cavallazzi et al. | |

(Continued)

OTHER PUBLICATIONS

Cenzi, R; Burlini, D; Arduin, L; et al. Mandibular Condyle Fractures: Evaluation of the Strasbourg Osteosynthesis Research Group Classification. The Journal of Craniofacial Surgery. 20(1): 24-8. 2009.

(Continued)

*Primary Examiner* — Eduardo C Robert
*Assistant Examiner* — Michelle C. Eckman

(57) ABSTRACT

A device for intramedullary fixation of mandibular condyle fractures is provided. This device includes a proximal screw portion and a distal peg portion. The screw portion includes threads and a taper at the proximal tip. The peg portion contains a taper at the distal end, it may be of circular or ovoid cross-sectional shape to accommodate variations in individual patient anatomy, and may contain peg holes oriented perpendicular to its long axis. Perpendicular grooves are present on the distal end of the device to allow coupling with a surgical screwdriver. The method of application includes reaming of the intramedullary canal, insertion of the device into the proximal condyle fragment, and manipulation of the intramedullary canal of the distal mandible onto the device to achieve stable fracture fixation. This device and method provide the benefits of intramedullary fixation and a total endoscopic surgical approach to the treatment of mandibular condyle fractures.

2 Claims, 4 Drawing Sheets

U.S. PATENT DOCUMENTS

| | | | | |
|---|---|---|---|---|
| 8,167,891 | B2* | 5/2012 | Terres et al. | 606/105 |
| 2003/0135214 | A1* | 7/2003 | Fetto et al. | 606/72 |
| 2006/0235414 | A1* | 10/2006 | Lim et al. | 606/73 |
| 2007/0233123 | A1* | 10/2007 | Ahmad et al. | 606/73 |
| 2008/0177291 | A1* | 7/2008 | Jensen et al. | 606/151 |
| 2008/0208261 | A1* | 8/2008 | Medoff | 606/280 |
| 2008/0221574 | A1* | 9/2008 | Cavallazzi et al. | 606/62 |
| 2008/0234675 | A1* | 9/2008 | Ohrnell et al. | 606/60 |
| 2009/0036893 | A1* | 2/2009 | Kartalian et al. | 606/60 |
| 2009/0210016 | A1* | 8/2009 | Champagne | 606/309 |
| 2010/0036439 | A1* | 2/2010 | Lavi | 606/308 |
| 2011/0009865 | A1* | 1/2011 | Orfaly | 606/62 |
| 2011/0060336 | A1* | 3/2011 | Pool et al. | 606/57 |
| 2011/0087227 | A1* | 4/2011 | Mazur et al. | 606/62 |
| 2011/0118740 | A1* | 5/2011 | Rabiner et al. | 606/63 |
| 2011/0160728 | A1* | 6/2011 | Blitz et al. | 606/64 |
| 2012/0065692 | A1* | 3/2012 | Champagne et al. | 606/311 |

OTHER PUBLICATIONS

Brandt, MT; Huag, RH. Open Versus Closed Reduction of Adult Mandibular Condyle Fractures: A Review of the Literature Regarding the Evolution of Current Thoughts on Management. Journal of Oral and Maxillofacial Surgery. 61: 1324-1332. 2003.

Schneider, M; Erasmus, F; Gerlach, KL; et al. Open Reduction and Internal Fixation Versus Closed Treatment and Mandibulomaxillary Fixation of Fractures of the Mandibular Condylar Process: A Randomized, Prospective, Multicenter Study with Special Evaluation of Fracture Level. Journal of Oral and Maxillofacial Surgery. 66: 2537-2544. 2008.

Tominaga, K; Habu, M; Khanal, A; et al. Biomechanical evaluation of different types of rigid internal fixation techniques for subcondylar fractures. J Oral Maxillofac Surg 64 (2006), p. 1510.

Ducic Y. Endoscopic treatment of subcondylar fractures. Laryngoscope. 118(7):1164-7, Jul. 2008.

Ellis, E; McFadden, D; Simon, P; et al. Surgical complications with open treatment of mandibular condylar process fractures. J. Oral Maxillofac. Surg. 58: 950, 2000.

Hammer, B; Schier, P; Prein, J. Osteosynthesis of condylar neck fractures: a review of 30 patients. British Journal of Oral & Maxillofacial Surgery. 35: 288-291, 1997.

Ziccardi, VB; Schneider RE; Kummer, FJ. Wurzburg lag screw plate versus four-hole miniplate for the treatment of condylar process fractures. J Oral Maxillofac Surg, 55; 602-607. 1997.

Frake, PC; Howell, RJ; Joshi, AS. Strength of titanium intramedullary implant versus miniplate fixation of mandibular condyle fractures. Otolaryngology Head & Neck Surgery, 147; 33-39. 2012.

Wagner, A; Krach, W; Schicho, K; et al. A 3-dimensional finite-element analysis investigating the biomechanical behavior of the mandible and plate osteosynthesis in cases of fractures of the condylar process. Oral Surg Oral Med Oral Pathol Oral Radiol Endod. 94:678-86. 2002.

Gealh, WC; Costa, JV; Ferreira, GM; Filho, LI. Comparative study of the mechanical resistance of 2 separate plates and 2 overlaid plates used in the fixation of the mandibular condyle: an in-vitro study. J Oral Maxillofac Surg 67:738-743, 2009.

Stephenson, KL; Graham, WC. The use of the Kirschner pin in fractures of the condyle. Plast Reconstr Surg. 10:19-22. 1952.

Hendrix, JH; Sanders, SG; Green, B. Open reduction of mandibular condyle. Plast Reconst Surg Transplant Bull. 23: 283-287. 1959.

* cited by examiner

INTRAMEDULLARY MANDIBULAR CONDYLE IMPLANTS AND METHOD FOR APPLICATION OF THE SAME

CROSS-REFERENCE To RELATED APPLICATIONS

This non-provisional United States utility patent application claims the benefit of the filing date of provisional U.S. utility patent application No. 61/335,820 with the filing date of Jan. 13, 2010, and is the non-provisional filing of the material contained therein.

STATEMENT REGARDING FEDERALLY SPONSORED RESEARCH OR DEVELOPMENT

This non-provisional United States utility patent application is not related to any federal research or federal funding.

REFERENCE to SEQUENCE LISTING, TABLE, OR APPENDIX

Not Applicable

BACKGROUND OF THE INVENTION

1. Field of Invention

This invention relates broadly to surgery and surgical devices. Particularly, this invention relates to intramedullary implants for fixation of fractures of the mandibular condyle and methods for using the same.

2. State of the Art

Fractures of the mandibular condyle are common, comprising almost a third of all mandible fractures. Treatment of mandibular fractures focuses on reduction of the fracture and rigid fixation to allow for osteosynthesis. This can be accomplished with maxillomandibular fixation, internal fixation, or both. Open reduction and internal fixation (ORIF) has become the preferred method of treatment for many mandibular fractures because it can restore the load-bearing properties of the bone and allow for a quicker return to function. This technique can be applied to fractures of the mandibular condyle through transcutaneous incisions or through an intraoral incision using endoscopes. Both of these approaches can provide adequate surgical access; however, each has its disadvantages.

External approaches carry the risk of injury to one or more branches of the facial nerve salivary fistula, Frey's syndrome, and hypertrophic scarring. Current ORIF techniques employ plates and screws applied to the external bone surface. It is difficult to apply the screws at the requisite 90 degree angle without a transbuccal puncture incision when using these plates. Improper screw placement, insufficient bone stock on the proximal fragment, and failure (bending or fracture) of the plate have been encountered with traditional miniplate implants.

Endoscopic mandibular condyle repair techniques have aided in the treatment of many condylar and subcondylar fractures in recent years. The use of endoscopes to apply traditional miniplates still requires a transbuccal puncture and carries the potential for facial nerve injury; however, there has been a much lower incidence of facial nerve paresis than in traditional "open" surgical approaches. Endoscopic repair is most readily applied to fractures that are in the subcondylar region, where there is adequate bone to hold two screws proximal and distal to the fracture line. However, this technique is more difficult to apply to fractures that are through the condylar neck, where it is more challenging to keep the fracture reduced, place the plate, and insert the screws properly due to the small size of the proximal bone fragment.

For these reasons, many surgeons opt to treat mandibular condyle fractures with extended maxillomandibular fixation; a treatment that is itself associated with potential morbidity including inadequate reduction of the fracture, discomfort, prolonged loss of function, joint ankylosis, risk of aspiration, and death.

Intramedullary fixation is a technique that has been utilized by orthopedic surgeons in the treatment of certain fractures of long tubular bones in the body including the femur, tibia, clavicle, and radius. Intramedullary fixation has been attempted in the mandibular condyle in the form of Kirschner wires (K-wire) inserted along the entire length of the mandibular ramus and condyle as well as lag screws drilled through cortical bone. As with intramedullary fixation of long bone fractures, previous attempts at intramedullary fixation of the mandibular condyle have relied on insertion of implants or a guide wire through healthy bone distant to the fracture (for example; through the epiphysis or through a joint). The anatomy of the face and jaw makes this technique impractical. Successful application of a K-wire to the mandibular condyle requires a submental neck incision and an intact and straight intramedullary canal. The intramedullary canal often does not meet these requirements due to the natural curvature of the ramus and variations in the intramedullary space. Furthermore, a K-wire has a smooth surface and does not engage either side of the fractured bone. Therefore, it does not actually provide fixation of the fracture. Lag screws do provide fixation of the fracture but require application through cortical bone, in some cases at an acute angle to the intramedullary axis of the bone. Furthermore, both K-wires and lag screws require facial or neck incisions (invasive approach) which increase the risk of surgical morbidity as previously discussed.

BRIEF SUMMARY OF THE INVENTION

It is an important object of the present invention to provide a treatment which provides stabilization and fixation of mandibular condyle fractures.

It is another object of the invention to provide an intramedullary implant that is constructed of biocompatible materials for such treatment.

It is another object of the invention to provide an implant that can be surgically implanted in a minimally invasive manner without incisions on the face or neck, requiring only an intraoral incision.

It is a further object of the invention to provide treatment of mandibular condyle fractures based on the individual patient's condyle anatomy, therefore multiple configurations of the implant are described.

In accord with these objects, which will be discussed in detail below, an intramedullary implant and method for surgical application of the same are provided. The implant is an elongate rod with a proximal and distal portion. The proximal portion contains screw threads and a tapered tip. The distal portion is circular or ovoid in cross-sectional shape and may contain holes extending perpendicular to the long axis of the rod. The distal tip contains a taper and grooves placed perpendicular to each other on the distal end for coupling with a surgical instrument of corresponding shape.

The method for positioning the implant inside of the intramedullary canal of the fractured mandibular condyle includes, after an endoscopic transoral approach to the mandibular condyle, (i) reaming of the contents of the intramedullary canal, (ii) screwing the implant into the proximal condyle fragment and disengaging the surgical instrument used to manipulate it, (iii) inferior retraction of the distal mandible by placement of a retractor at the sigmoid notch, (iv) manipulating the distal mandible on to the implant already in place in the proximal condyle fragment, and (v) application of pressure at the angle of the mandible to completely reduce the fracture.

The method enables implantation of the device in a minimally invasive manner that provides fixation of a fractured mandibular condyle utilizing the intramedullary space without the need for incisions on the face or neck.

The method is additionally unique in that it is the first to apply an intramedullary implant to the mandibular condyle through the fracture site without violating otherwise healthy cortical bone of the condylar head or the mandibular angle or ramus.

Those skilled in the art will appreciate additional objects and advantages of the invention upon reference to the detailed description taken in conjunction with the provided figures.

DETAILED DESCRIPTION OF THE INVENTION

Figure 1:
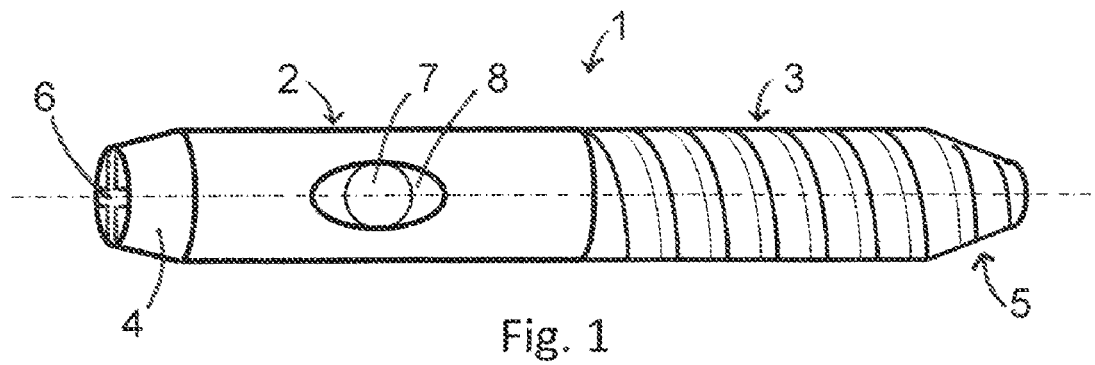
FIG. 1 is a top view of an embodiment of the intramedullary implant of the invention.
Figure 2:
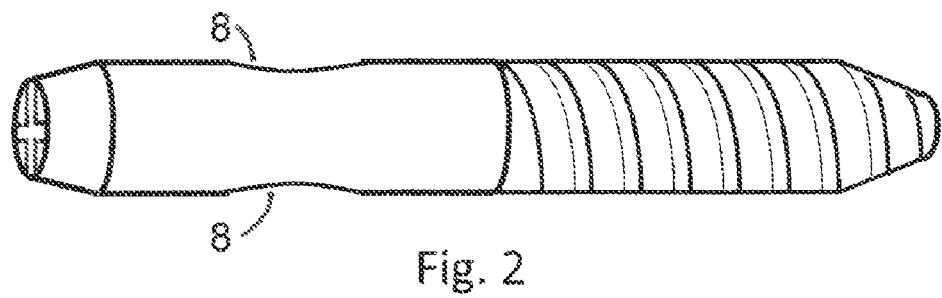
FIG. 2 is a side view of an embodiment of the intramedullary implant of the invention.
Figure 3:
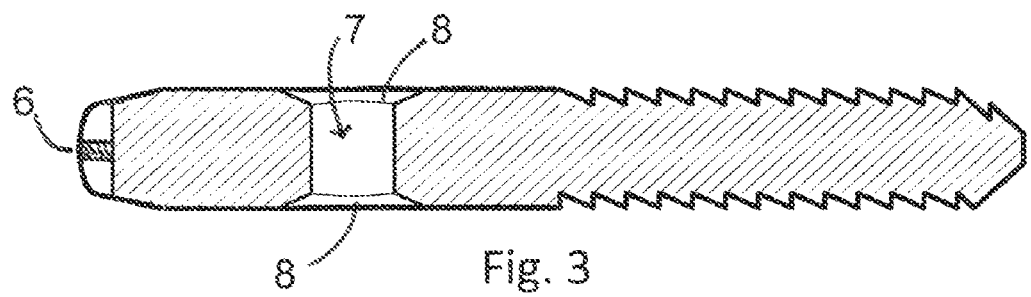
FIG. 3 is a longitudinal section of the of the intramedullary implant of the invention shown in FIG. 1.

Turning now to FIGS. 1 through 3, a preferred intramedullary implant 1 for use according to a preferred application of a preferred system and method of the invention is provided. The implant 1 is preferably made of biocompatible material, e.g., stainless steel, titanium, polymers, or biodegradable material, and includes a distal peg portion 2 and a proximal screw portion 3. The ends 4, 5 of the rod are tapered. The distal end 4 tapers to a flat surface in which perpendicular channels 6 are present to allow the coupling of a surgical instrument or screwdriver to the device. The proximal end 5 tapers to a rounded point and contains screw threads in continuity with those present on the proximal shaft 3. The shaft of the distal portion 2 comprises an elongate rod which includes one hole 7 along the rod 2. This hole 7 extends perpendicularly through the rod 2. Hole 7 includes an upper and lower recess 8 to facilitate engagement with a separate perpendicularly oriented bone screw to provide further fixation including prevention of rotation and longitudinal displacement of the device once implanted in vivo.

Figure 4:
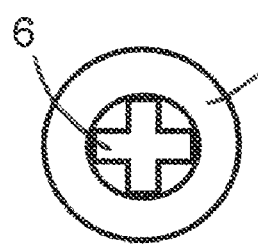
FIG. 4 is a distal end view of the intramedullary implant of the invention with a circular cross-sectional design.
Figure 5:
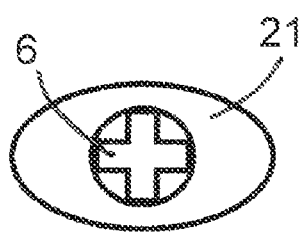
FIG. 5 is a distal end view of the intramedullary implant of the invention with an ovoid cross-sectional design.

Referring now to FIGS. 4 and 5, end views of the distal end of the implant, two options for the cross-sectional shape of the distal peg portion 2 are presented. FIG. 4 demonstrates the distal peg portion 2 having a circular cross-sectional shape 20, and FIG. 5 demonstrates the distal peg portion 2 having an ovoid cross-sectional shape 21. It is noted that the two options for cross-sectional shape 20, 21 of the distal peg portion 2 of the implant are presented to allow the surgeon to choose which shape would best fit in an individual patient's intramedullary space. In both of these configurations of the device, the proximal screw portion 3 would be circular in cross-section.

Figure 6:
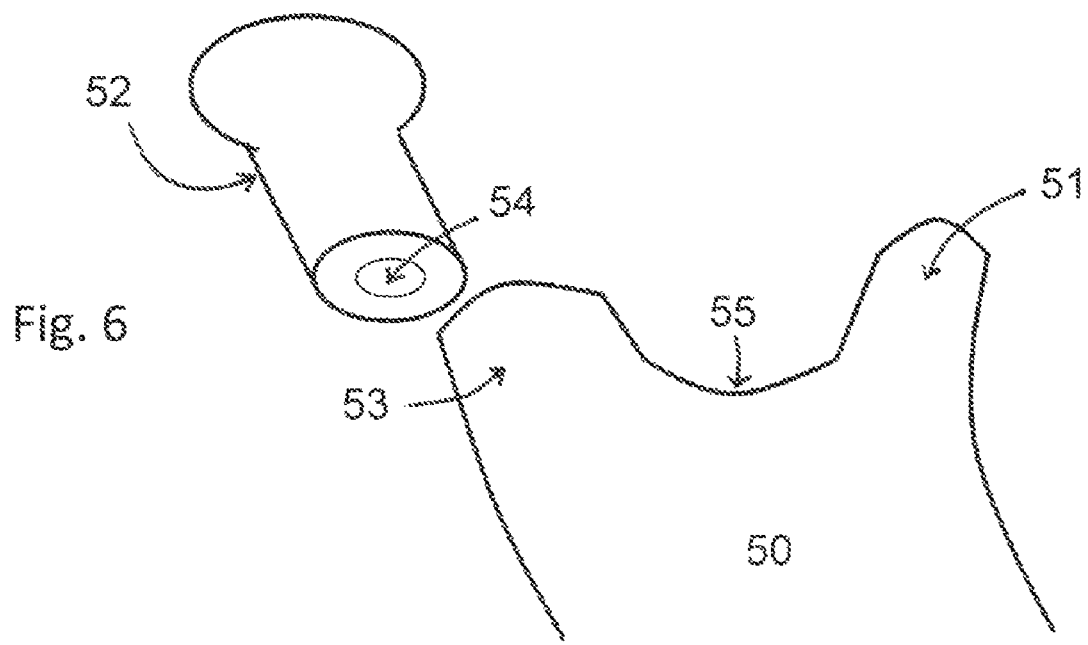
FIG. 6 is a side view of the ramus and condyle segments of the right side of the human mandible separated by a discontinuity representing a condylar fracture.

In view of the above descriptions of the intramedullary condyle implant, a preferred method for surgically inserting the device 1 inside the intramedullary canal of a fractured mandibular condyle according to the invention is now described. Referring now to FIG. 6, a standard endoscopic approach to the mandibular condyle is performed, including an incision in the buccal mucosa and subperiosteal dissection along the ramus and condyle of the mandible. Once the fracture is adequately exposed, the relevant anatomy will be visible within the endoscopic optical pocket. This anatomy is represented in a lateral view in FIG. 6. A portion of the right side of the mandible is represented including the mandibular ramus 50, the coronoid process 51, the proximal condylar neck fragment 52, the distal condylar neck fragment 53, the intramedullary canal of the mandibular condyle 54, and the sigmoid notch 55.

Figure 7:
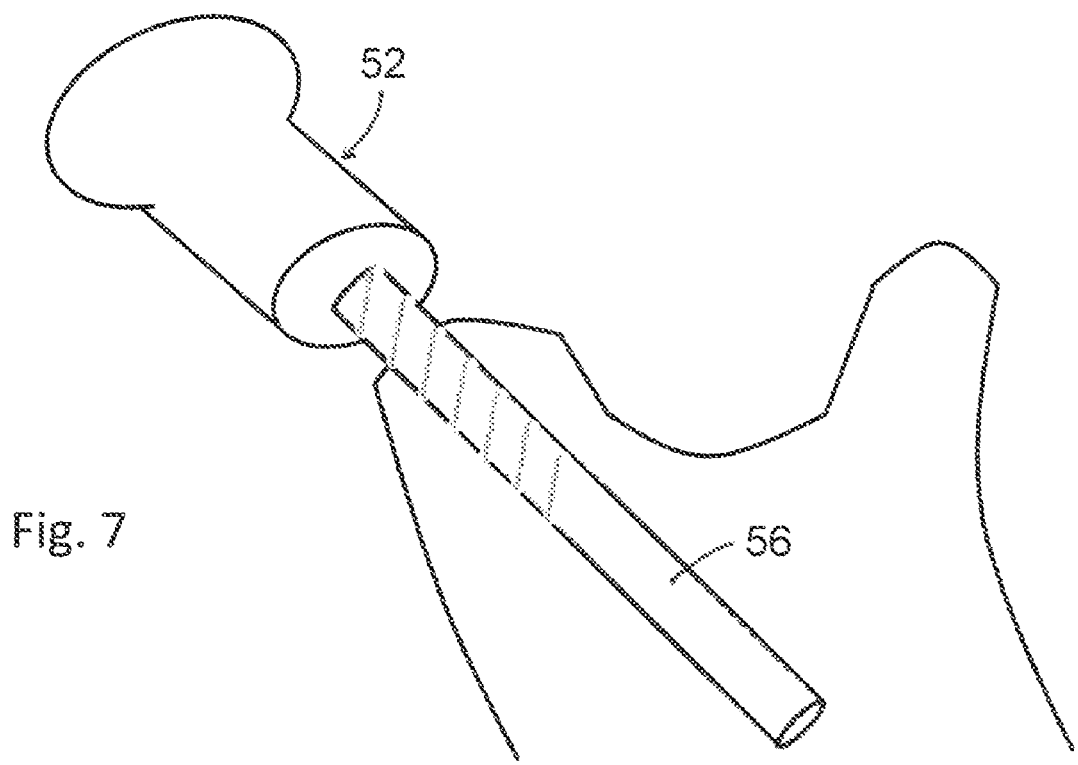
FIGS. 7-10 illustrate a method of implanting an intramedullary condyle fixation device according to the invention.

Referring to FIG. 7, a drill bit 56 is inserted perpendicular to the ramus of the mandible and into the intramedullary canal or the proximal condylar neck fragment 52. Gentle finger twisting of the drill bit provides enough force to remove the marrow and other contents of the intramedullary canal without damaging the adjacent cortical bone.

Figure 8:
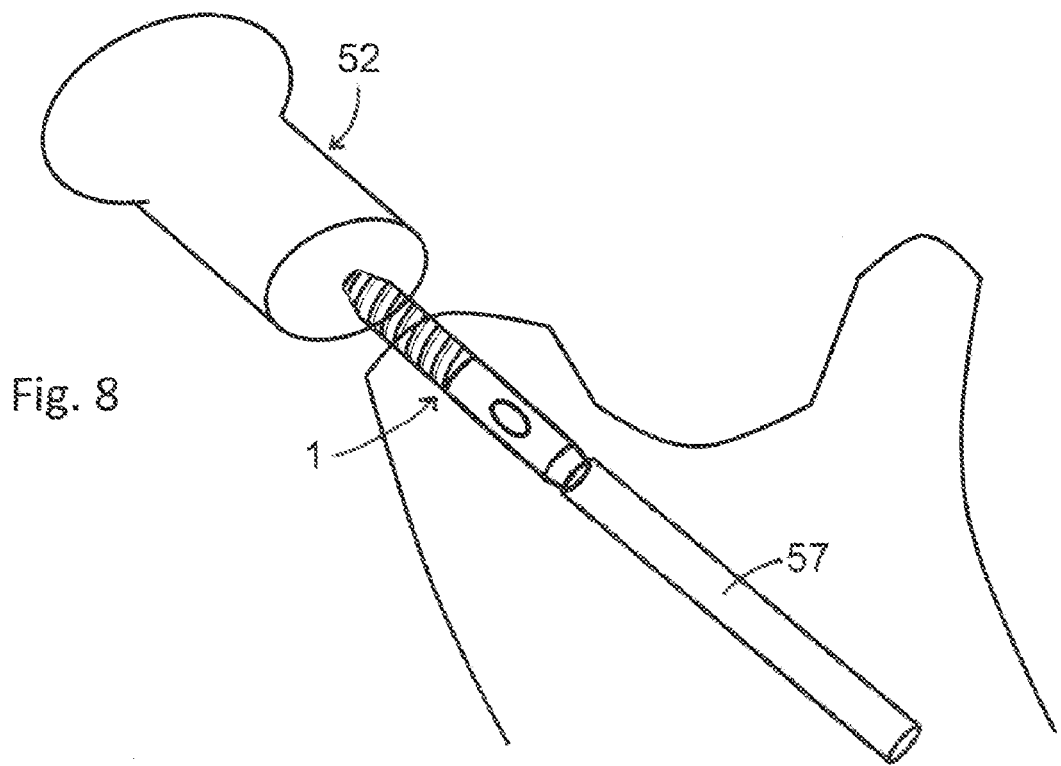

Referring now to FIG. 8, the intramedullary condyle implant 1 is introduced into the surgical field coupled to a surgical screwdriver 57 through the intraoral incision. The intramedullary condyle implant 1 is then inserted into the intramedullary canal of the proximal condylar neck fragment 52. The proximal screw portion 3 of the device is then screwed into place in the proximal condylar neck fragment 52. Once this is complete, the surgical screwdriver is disengaged and removed from the field.

Figure 9:
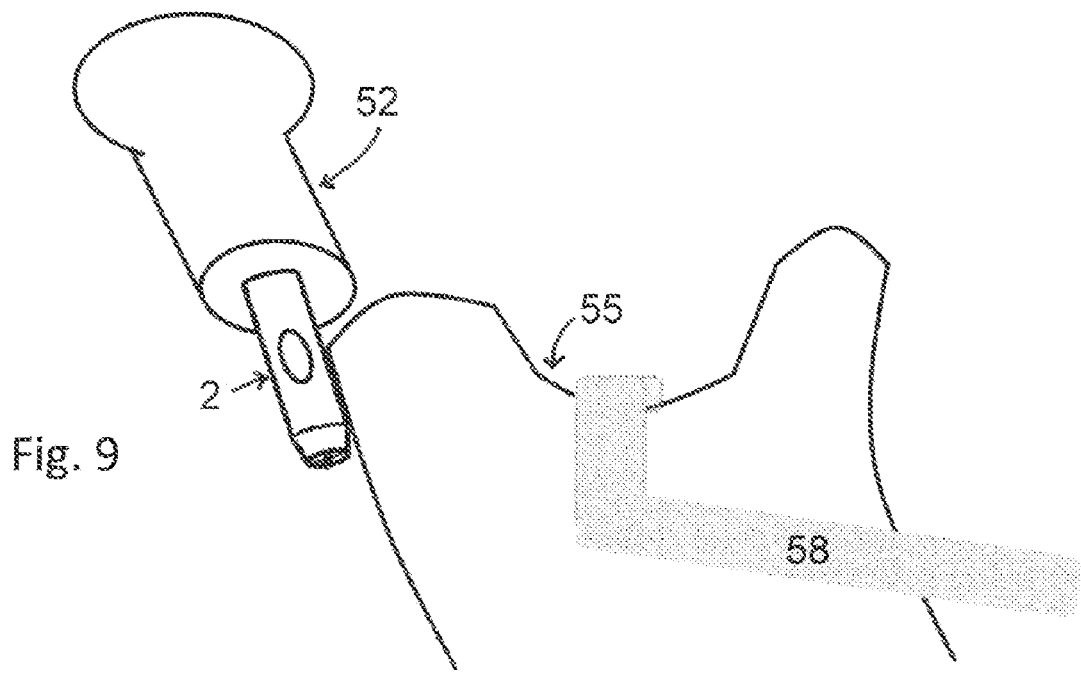

Referring now to FIG. 9, the distal peg portion of the implant 2 can be seen protruding from the proximal condylar neck fragment 52. A surgical retractor 58 is placed onto the sigmoid notch 55 of the mandible and inferiorly directed retraction is applied. This displaces the distal mandible below the level of the protruding distal peg portion 2 of the implant. The implant is then positioned directly superior to the distal intramedullary canal and the inferior retraction on the sigmoid notch is released. Gentle superiorly directed pressure is then applied to the angle of the mandible using the operator's hand and superior displacement is induced causing the distal peg portion of the implant 2 to enter the distal intramedullary canal and reduce the fracture.

Figure 10:
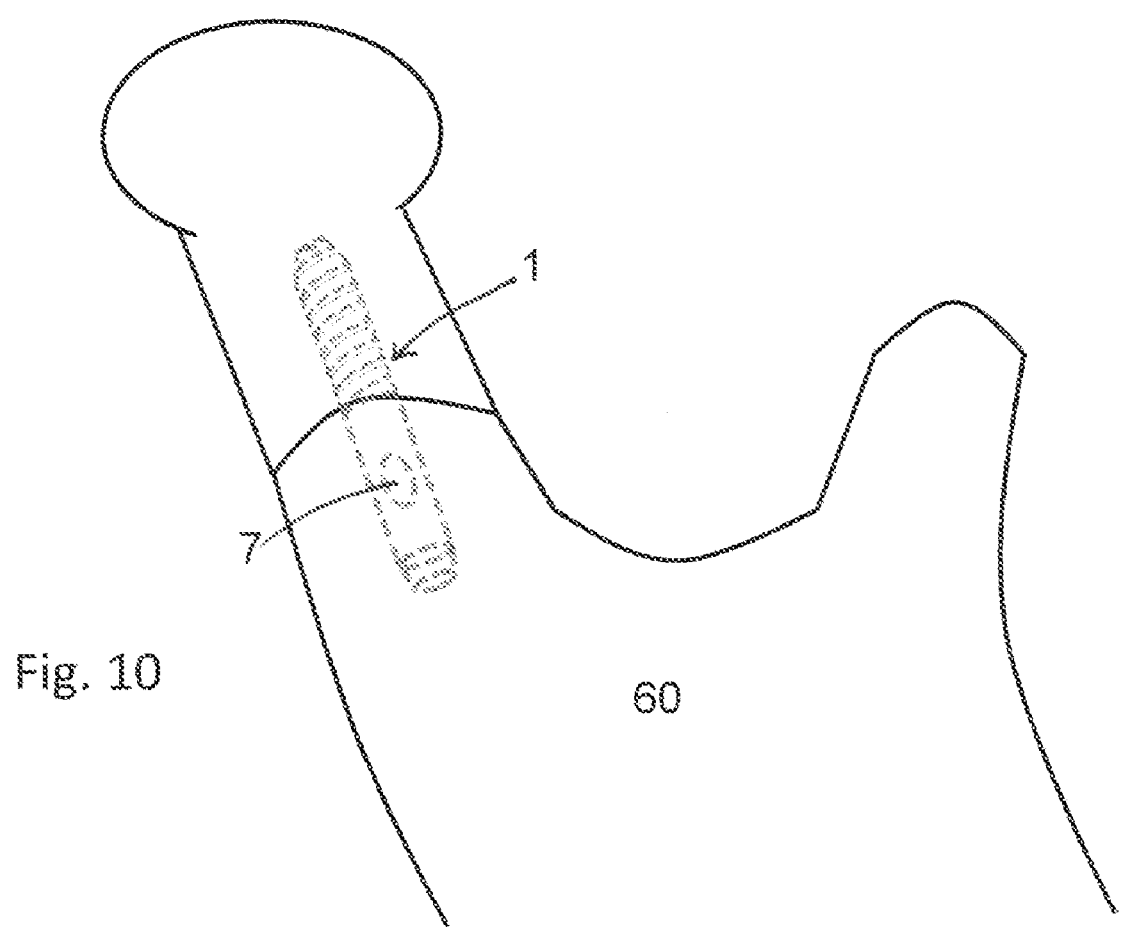

Referring now to FIG. 10, the fracture is now reduced and dashed lines represent the profile of the intramedullary implant 1 within the condylar bone to demonstrate its final position within the intramedullary space spanning the fracture. Once this has been accomplished a perpendicular bone screw may be applied through hole 7 for further fixation of the implant if this is deemed necessary by the surgeon based on individual patient factors.

In accord with other aspects of the method of the invention, once the intramedullary implant is so positioned within the proximal and distal fragments of the condyle, the fracture is reduced and rigid internal fixation is achieved. In summary, the preferred method for inserting the intramedullary condyle implant includes (i) reaming of the contents of the intramedullary canal, (ii) screwing the implant into the proximal condyle fragment and disengaging the screwdriver used to manipulate it, (iii) inferior retraction of the distal mandible by placement of a retractor at the sigmoid notch, (iv) manipulating the distal mandible on to the implant already in place in the proximal condyle fragment, and (v) applying pressure at the angle of the mandible to completely reduce the fracture. It is within the scope of the invention to secure the intramedullary condyle implant with or without the use of a perpendicularly oriented bone screw for additional fixation of the implant.

The method enables implantation of an intramedullary condyle bone fracture fixation device in a manner that provides the benefits of both rigid internal fixation and a total endoscopic approach; i.e., restoration of load bearing properties of the bone, earlier return to masticatory function, avoidance of facial incisions and the potential morbidity associated with traditional "open" surgical approaches including, but not limited to, facial nerve injury, and facial scarring. In addition, referring to FIG. 10, the method provides for excellent reduction of the fracture and rigid immobilization and internal fixation.

Herein there have been illustrated and described several embodiments of an intramedullary mandibular condyle implant and a method for repairing a mandibular condyle fracture with said implant. It is not intended that the invention be limited to the particular embodiments of the invention that have been described, but it is intended that the invention be as broad in scope as the art allows and that specification be read as such. While a particular implant is described within this specification with respect to applying the method of the invention, it is understood that other embodiments of an implant may also be used. As an example, and not by way of limitation, the implant used in the method may have a variety of dimension combinations, cross-sectional shapes of the distal peg portion, and a number of perpendicular screw holes to allow for adaptation to individual patient anatomy. Therefore, those skilled in the art will appreciate that other modifications could be made to the provided invention without deviating from the invention's spirit and scope as claimed.

What is claimed is:

1. A method of treating a fracture of a mandibular condyle of a mandible, said fracture having proximal and distal fragments and each fragment including an intramedullary canal, said method comprising the steps of:
   a) providing an intramedullary condyle implant having a threaded proximal end portion and a distal peg end portion;
   b) reaming the intramedullary canal of said proximal fragment of the condyle;
   c) screwing said threaded proximal end portion of the intramedullary condyle implant into the reamed intramedullary canal of said proximal fragment;
   d) disengaging a surgical instrument used to manipulate the intramedullary condyle implant from said implant;
   e) placing a retractor at the mandibular sigmoid notch adjacent said fracture of the mandibular condyle, and retracting said distal fragment;
   f) applying pressure at the angle part of said mandible to completely reduce the fracture and guide said distal peg end portion of the intramedullary condyle implant into the intramedullary canal of the distal portion of the mandibular condyle.

2. The method of claim 1, further including inserting a cross-locking screw or pin through a perpendicular hole in said distal peg end portion of the intramedullary condyle implant.

* * * * *